US008725452B2

(12) United States Patent
Han

(10) Patent No.: US 8,725,452 B2
(45) Date of Patent: May 13, 2014

(54) METHOD OF CONFIRMING MOTION PARAMETERS APPARATUS FOR THE SAME, AND MOTION ASSISTING DEVICE

(75) Inventor: Zheng Han, Beijing (CN)

(73) Assignee: Zepp Labs, Inc., Los Gatos, CA (US)

(*) Notice: Subject to any disclaimer, the term of this patent is extended or adjusted under 35 U.S.C. 154(b) by 362 days.

(21) Appl. No.: 13/269,236

(22) Filed: Oct. 7, 2011

(65) Prior Publication Data

US 2012/0278023 A1 Nov. 1, 2012

(30) Foreign Application Priority Data

Apr. 29, 2011 (CN) .......................... 2011 1 0111559

(51) Int. Cl.
*G01C 9/00* (2006.01)
(52) U.S. Cl.
USPC .......................................................... 702/152
(58) Field of Classification Search
USPC .......................................................... 702/152
See application file for complete search history.

(56) References Cited

U.S. PATENT DOCUMENTS

| 8,523,696 B2 * | 9/2013 | Kamino et al. ............... 473/131 |
| 8,538,722 B2 * | 9/2013 | Naya ............................. 702/141 |

FOREIGN PATENT DOCUMENTS

| CN | 101299271 | 11/2008 |
| CN | 101488222 | 7/2009 |
| CN | 101886927 | 11/2010 |
| CN | 101964047 | 2/2011 |
| CN | 102184549 | 9/2011 |
| WO | 2007124257 | 11/2007 |

OTHER PUBLICATIONS

Office Action issued on Jun. 4, 2012 for a related AU Patent Application No. 2011244873.
Office Action issued on Apr. 19, 2012 for a related CN Patent Application No. 201110111559.8 and its English summary provided by the clients.
IRPR/WO for related PCT/CN2012/074748 mailed on Aug. 9, 2012 and its English translation.
ISR for related PCT/CN2012/074748 mailed on Aug. 9, 2012 and its English translation.

* cited by examiner

Primary Examiner — Stephen Cherry
(74) Attorney, Agent, or Firm — Ladas & Parry, LLP

(57) ABSTRACT

The invention provides a method of confirming motion parameters, an apparatus for the same, and a motion assisting device. The invention obtains and utilizes the motion data of a recognized object sampled at each of the sampling time, comprising the acceleration of the recognized object sampled by a tri-axial accelerometer, the angular velocity of the recognized object sampled by a tri-axial gyroscope, and the angle of the recognized object corresponding to a three-dimensional geomagnetic coordinate system sampled by a tri-axial magnetometer. Feedback calculation is utilized to obtain an actual acceleration at each sampling time from the motion original time to the motion end time, and the actual acceleration is obtained by reducing the acceleration of gravity from the acceleration sampled by a tri-axial accelerometer. The invention reduces the complexity of the system, and the accuracy is less affected by environmental factors, particularly light.

29 Claims, 4 Drawing Sheets

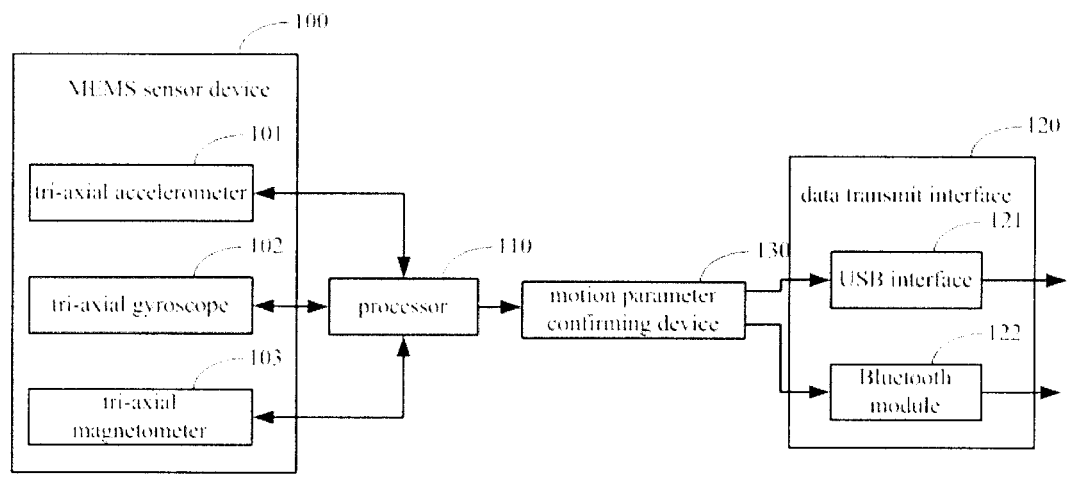
FIG.1b
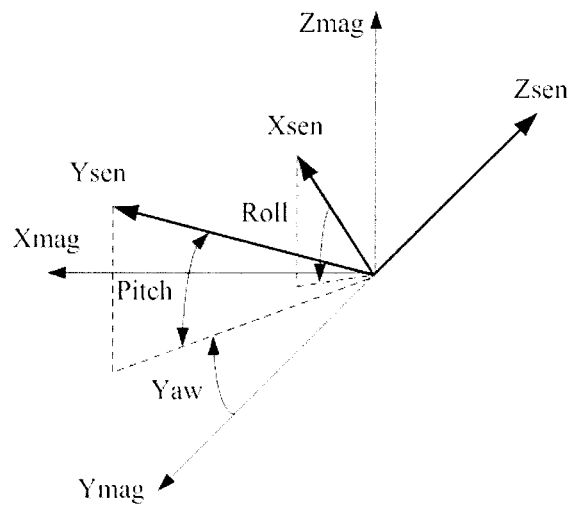
FIG.2
| header field | mark field | motion data sampled by tri-axial magnetometer | motion data sampled by tri-axial accelerometer | motion data sampled by tri-axial gyroscope |
FIG.3

METHOD OF CONFIRMING MOTION PARAMETERS APPARATUS FOR THE SAME, AND MOTION ASSISTING DEVICE

CROSS-REFERENCE TO RELATED APPLICATIONS

This application claims priority to Chinese Patent Application No. 201110111559.8 filed on Apr. 29, 2011, the disclosure of which is incorporated herein by reference.

FIELD OF THE DISCLOSURE

The present disclosure relates to motion recognition technology, and particularly to a method of confirming motion parameters, an apparatus for the same, and a motion assisting device.

BACKGROUND OF THE DISCLOSURE

Path and stance recognition for a spatial accelerated motion refers to detecting position and intersection angles at each time in the moving process of an object, and obtaining the real-time velocity of the object. The technique of path and stance recognition for the spatial accelerated motion can be widely applicable in combination to human body action for detection of human body action in areas such as sports, games, movie technology, medical surgery simulation or action skill training.

Currently, the existing motion recognition technology focuses on the following issues:

(1) utilizing a combination of ultrared array and microelectromechanical system (MEMS) sensors to detect a three-dimensional motion.

(2) utilizing a combination of visual and MEMS sensors to enhance accuracy to motion recognition to a hand motion.

(3) utilizing visualization methods to sample information including full-body three-dimensional motions, facial motions and voice by using RGB cameras, depth sensors and microphone arrays.

However, the three focused issues utilize visualization methods, and accuracy would be greatly affected by environmental factors, particularly light.

SUMMARY OF THE DISCLOSURE

The disclosure provides a method of confirming motion parameters, an apparatus for the same, and a motion assisting device, for maintaining the accuracy by reducing the effect of environmental factors.

Specifically, the method of confirming motion parameters provided by the disclosure comprises:

(S1) obtaining and storing motion data at each sampling time, the motion data comprising: acceleration of a recognized object, angular velocity of the recognized object, and an angle of the recognized object corresponding to a three-dimensional geomagnetic coordinate system;

(S2) perform ling motion static detection utilizing the acceleration stored at each of the sampling time to confirm a motion original time $t_o$ and a motion end time $t_e$ of a motion;

(S3) confirming an original stance matrix $T_m^{bInit}$ corresponding to the three-dimensional geomagnetic coordinate system at the motion original time $t_o$ according to the angle stored at the motion original time $t_o$; and (S4) using each of the sampling time sequentially as a current sampling time to perform steps S41 to S43:

(S41) confirming and recording a stance change matrix $T_{bInit}^{bCur}$ from the current sampling time to the motion original time $t_o$ according to the angular velocity stored at the current sampling time and at a previous sampling time, and a stance change matrix $T_{bInit}^{bPre}$ from the previous sampling time to the motion original time $t_o$;

(S42) confirming a stance matrix $T_m^{bCur}$ at the current sampling time corresponding to the three-dimensional geomagnetic coordinate system as $T_m^{bCur} = T_{bInit}^{bCur}$; and (S43) obtaining an actual acceleration $a_m^{Mcur}$ at the current sampling time by adjusting the acceleration $a^{Cur}$ at the current sampling time utilizing the stance matrix $T_m^{bCur}$ to reduces an acceleration of gravity $\vec{g}$ from the acceleration $a^{Cur}$ at the current sampling time.

The apparatus for confirming motion parameters provided by the disclosure comprises:

a motion data obtaining unit to obtain motion data at each sampling time of a motion, the motion data comprising: acceleration of a recognized object sampled by a tri-axial accelerometer, angular velocity of the recognized object sampled by a tri-axial gyroscope, and an angle of the recognized object corresponding to a three-dimensional geomagnetic coordinate system sampled by a tri-axial magnetometer;

a data storage unit to store the motion data;

a motion static detecting unit to perform motion static detection utilizing the acceleration stored in the data storage unit at each of the sampling time to confirm a motion original time $t_o$ and a motion end time $t_e$ of the motion;

an original stance confirming unit to confirm an original stance matrix $T_m^{bInit}$ corresponding to the three-dimensional geomagnetic coordinate system at the motion original time $t_o$ according to the angle stored in the data storage unit at the motion original time $t_o$; and a motion parameter confirming unit to confirm the acceleration at each of the sampling time by using the sampling time after the motion original time $t_o$ and before the motion end time $t_e$ sequentially as a current sampling time; wherein the motion parameter confirming unit comprises:

a stance change confirming module to confirm and record a stance change matrix $T_{bInit}^{bCur}$ from the current sampling time to the motion original time $t_o$ according to the angular velocity stored in the data storage unit at the current sampling time and at a previous sampling time, and a stance change matrix $T_{bInit}^{bPre}$ from the previous sampling time to the motion original time $t_o$;

a real-time stance confirming module to confirm a stance matrix $T_m^{bCur}$ at the current sampling time corresponding to the three-dimensional geomagnetic coordinate system as $T_m^{bCur} = T_{bInit}^{bCur}$; and a degravitation module to obtain an actual acceleration $a_m^{Mcur}$ at the current sampling time by adjusting the acceleration $a^{Cur}$ at the current sampling time utilizing the stance matrix $T_m^{bCur}$ to reduces an acceleration of gravity $\vec{g}$ from the acceleration $a^{Cur}$ at the current sampling time.

The motion assisting device provided by the invention comprises a sensor device, and the aforementioned apparatus for confirming motion parameters.

The sensor device is configured to sample the motion data of the recognized object at each of the sampling time, the motion data comprising: the acceleration of the recognized object, the angular velocity of the recognized object, and the angle of the recognized object corresponding to a three-dimensional geomagnetic coordinate system.

According to the disclosed technology, the method, apparatus and the motion assisting device in the present disclosure do not rely on visualization methods, and the accuracy would be less affected by environmental factors, particularly light.

To improve understanding of the invention, the techniques employed by the present disclosure to achieve the foregoing objectives, characteristics and effects thereof are described hereinafter by way of examples with reference to the accompanying drawings.

BRIEF DESCRIPTION OF THE DRAWINGS

FIG. 1b is a schematic view of the motion assisting device in an embodiment of the disclosure;

FIG. 2 is a schematic view of an angle output by a tri-axial magnetometer in an embodiment of the disclosure;

FIG. 3 is a schematic view of the format of a data packet transmitted by a processor in an embodiment of the disclosure;

DETAILED DESCRIPTION OF THE DISCLOSURE

To achieve the foregoing objectives, technical characteristics and advantages, the techniques employed by the present disclosure are described hereinafter in detail by way of embodiments with reference to the accompanying drawings.

Figure 1A:
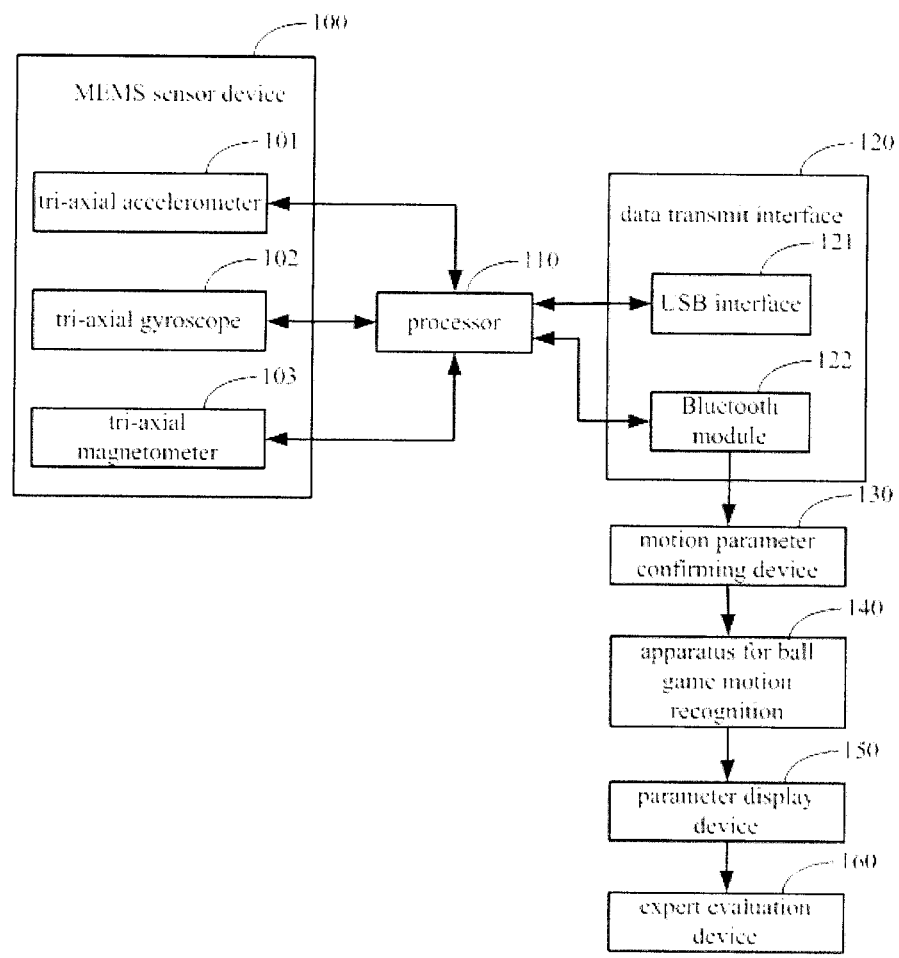
FIG. 1a is a schematic view of the structure of the recognition system in an embodiment of the disclosure.

An embodiment of the disclosure is shown in FIG. 1a as a recognition system, which comprises: a microelectromechanical system (MEMS) sensor device 100, a processor 110, data transmit interface 120, and an apparatus for confirming motion parameter 130. The recognition system can further comprise: a motion recognizing device 140, a parameter display device 150, and an expert evaluation device 160. The MEMS sensor device 100, the processor 110, and the data transmit interface 120 can be packed as a terminal device provided on the recognized object. For example, the MEMS sensor device 100, the processor 110, and the data transmit interface 120 can be packed as a portable motion detection device provided on the recognized object, such as the gloves of a ball player, the golf club, or a joint point. Generally, the weight of the portable motion detection device can be dozens of grams and thus ignorable without disturbing the motion of the recognized object.

In the embodiment, the MEMS sensor device 100 may comprise a tri-axial accelerometer 101, a tri-axial gyroscope 102, and a tri-axial magnetometer 103.

The tri-axial accelerometer 101 is configured to sample acceleration of the recognized object at each sampling time. The acceleration is the three-dimensional acceleration, which includes acceleration along X-axis, Y-axis and Z-axis at each sampling time.

The tri-axial gyroscope 102 is configured to sample angular velocity of the recognized object at each sampling time. Similarly, the angular velocity is the three-dimensional angular velocity, which includes angular velocity along X-axis, Y-axis and Z-axis at each sampling time.

The tri-axial magnetometer 103 is configured to sample the angle of the recognized object corresponding to a three-dimensional geomagnetic coordinate system. At each sampling time, the angle data include: Roll, Yaw and Pitch, in which Roll is the angle between the X-axis of the recognized object and the XY plane of the three-dimensional geomagnetic coordinate system, Yaw is the angle between the projecting vector of the Y-axis of the recognized object onto the XY plane of the three-dimensional geomagnetic coordinate system and the Y-axis of the three-dimensional geomagnetic coordinate system, and Pitch is the angle between the Y-axis of the recognized object and the the XY plane of the three-dimensional geomagnetic coordinate system. As shown in FIG. 2, Xmag, Ymag and Zmag are the X-axis, Y-axis and Z-axis of the three-dimensional geomagnetic coordinate system, and Xsen, Ysen and Zsen are the X-axis, Y-axis and Z-axis of the recognized object.

The processor 110 retrieves motion data sampled by the tri-axial accelerometer 101, the tri-axial gyroscope 102, and the tri-axial magnetometer 103 of the MEMS sensor device 100, and transmit the motion data to the motion parameter confirming device 130 according to predetermined transfer protocol. FIG. 3 shows one format of the data packet of the motion data transmitted by the processor, in which the mark field can include verification information to ensure the completeness and safety of the data, and the header field can include protocol header applied in transmission of the motion data.

Furthermore, the processor 110 can be utilized to receive configuration instructions from the data transmit interface 120, interpret the configuration instructions, configure the MEMS sensor device 100 according to the interpreted data, such as sampling accuracy, sampling frequency and range, and perform calibration of the motion data received. Preferably, the processor 110 can be a low power processor to increase endurance time.

The tri-axial accelerometer 101, the tri-axial gyroscope 102, and the tri-axial magnetometer 103 of the MEMS sensor device 100 can be connected to the processor 110 by serial bus or AD interface.

The data transmit interface 120 can support wired communication or wireless communication. Wired interface can be protocols such as USB, COM, LPT, or live line, and wireless interface can be Bluetooth or IRDA. In FIG. 1a, the data transmit interface 120 of the embodiment has a USB interface 121 and/or a Bluetooth module 122. The USB interface 121 can enable power charge of the terminal device with the MEMS sensor device 100, the processor 110, and the data transmit interface 120 packed together and perform two-way communication to other devices. The Bluetooth module 122 can enable two-way communication from the terminal device to the Bluetooth master device.

The apparatus for confirming motion parameter 130, the motion recognizing device 140, the parameter display device 150, and the expert evaluation device 160 can be connected to the processor 110 via the USB interface (not shown in FIG. 1a), or can serve as the Bluetooth master device and be connected to the processor 110 via the Bluetooth module 122.

The apparatus for confirming motion parameter 130 is configured to confirm motion parameters, such as acceleration information, velocity information, position information, and stance information, according to the motion data received.

The motion recognizing device 140 can be utilized to recognize the type of the motion according to the motion parameters confirmed by the apparatus for confirming motion parameter 130, and to extract the motion parameters of the motion of a certain type of sport.

The parameter display device 150 is configured to display the motion parameters confirmed by the apparatus for confirming motion parameter 130 in a certain format (the connection is not shown in the figures) or the motion parameters extracted by the motion recognizing device 140 in a certain format, such as showing a three-dimensional path of the position of the recognized object, or velocity information of the recognized object in the format of a table or a line chart. The parameter display device 150 can be any terminal device with display function, such as a computer, a cell phone, or a PDA.

The expert evaluation device 160 is configured to evaluate the motion according to the motion parameters confirmed by the apparatus for confirming motion parameter 130 (the connection is not shown in the figures) or the motion parameters extracted by the motion recognizing device 140. The evaluation can be from a real expert or an automated evaluation according to preset motion parameter database.

It should be noted that, in an embodiment, the MEMS sensor device 100 and the apparatus for confirming motion parameter 130 can be packed as a motion assisting device, as shown in FIG. 1b. The apparatus for confirming motion parameter 130 can directly obtain the motion data sampled by the MEMS sensor device 100 and confirm the motion parameters of the recognized object at each of the sampling time, and transmit the motion parameters to the motion recognizing device 140 to perform motion recognition.

In the motion assisting device, the processor 110 can also retrieve the motion data from the MEMS sensor device 100 according to a predetermined frequency, and transmit the motion data to the apparatus for confirming motion parameter 130 under the transfer protocol.

Furthermore, the data transmit interface 120 can be provided as an interface to connect to the apparatus for confirming motion parameter 130. Similarly, the data transmit interface 120 can also be a USB interface 121 or a Bluetooth module 122. The data transmit interface 120 can transmit the motion parameters confirmed by the apparatus for confirming motion parameter 130 to other devices, such as the motion recognizing device, the parameter display device or the expert evaluation device.

Alternatively, the data transmit interface 120 can also be disposed between the processor and the apparatus for confirming motion parameter 130 in the way as shown in FIG. 1a.

Figure 4:
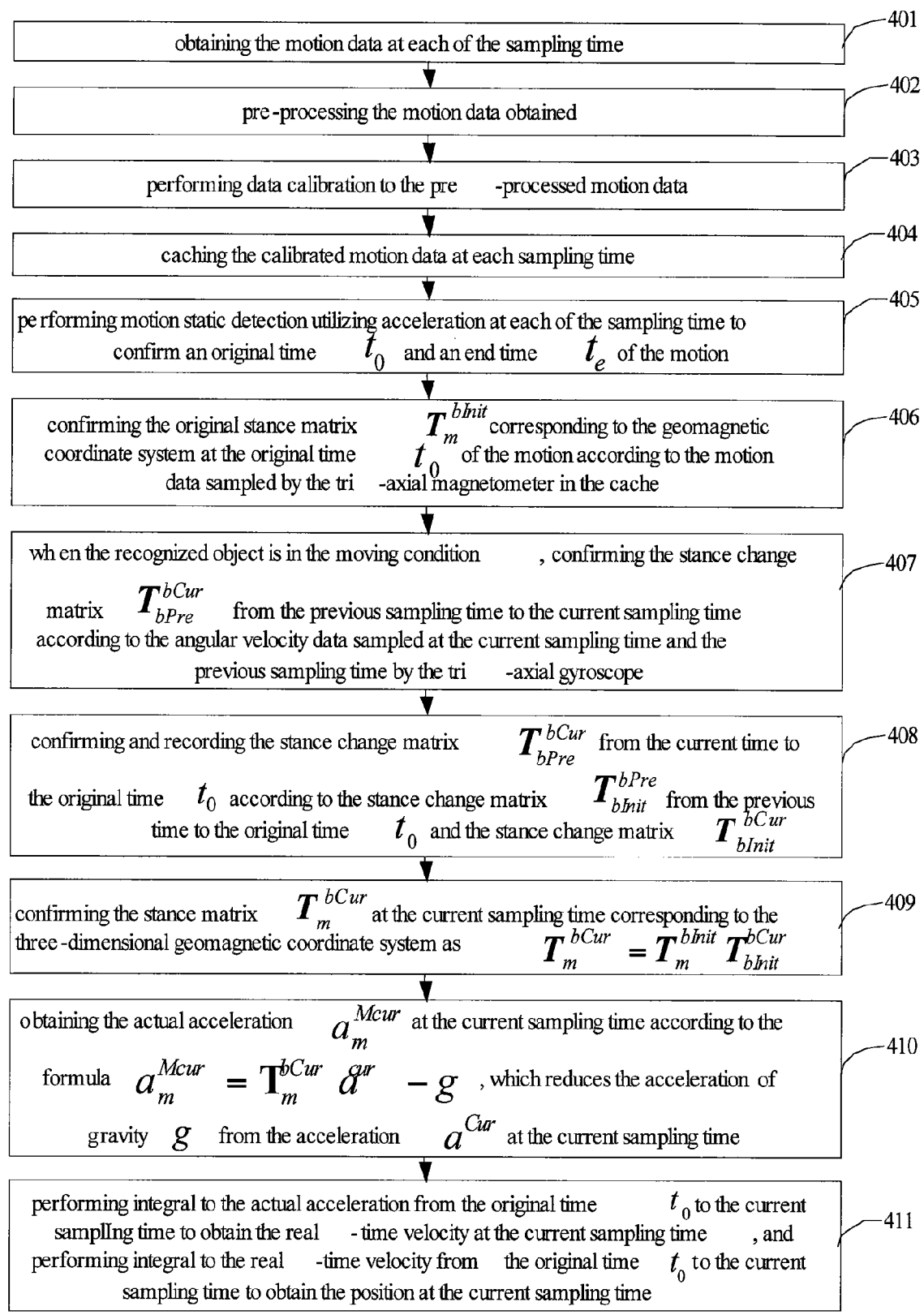
FIG. 4 is a flowchart of the method of confirming motion parameters provided in an embodiment of the disclosure.

Based on the aforementioned system, the method of confirming motion parameters utilized in the apparatus for confirming motion parameters 130 can be described according to the following embodiment. As shown in FIG. 4, the method of confirming motion parameters comprises the following steps:

Step 401: obtaining the motion data at each of the sampling time, the motion data includes: the acceleration of the recognized object sampled by the tri-axial accelerometer, the angular velocity of the recognized object sampled by the tri-axial gyroscope, and the angle of the recognized object corresponding to a three-dimensional geomagnetic coordinate system sampled by the tri-axial magnetometer.

In obtaining the motion data at each sampling time, if the sampling frequency of the MEMS sensor device is not high enough, the motion data obtained can be processed by interpolation processing, such as linear interpolation or spline interpolation, to enhance the calculation accuracy of the motion parameters of acceleration, velocity and position.

Step 402: pre-processing the motion data obtained.

The pre-processing of the step is to perform filtering to the motion data to reduce the noise of the motion data sampled by the MEMS sensor device. Various filtering approaches can be utilized. For example, 16 point Fast Fourier Transform (FFT) filtering can be used. The specific approach of filtering is not limited.

The interpolation processing and pre-processing are not necessarily performed in a fixed order. The processing can be performed in any sequence. Alternatively, it is optional to perform only one of the processing.

Step 403: performing data calibration to the pre-processed motion data.

The step mainly performs calibration to the acceleration sampled by the tri-axial accelerometer. The tri-axial accelerometer has a zero drift $\vec{\omega}_o$, and the acceleration obtained at each sampling time is reduced by the zero drift $\vec{\omega}_o$ to obtain the calibrated acceleration at each sampling time. The zero drift $\vec{\omega}_o$ of the tri-axial accelerometer can be obtained by sampling acceleration to a nonmoving object.

The steps 402 and 403 are preferred steps of the embodiment of the invention. However, the steps 402 and 403 can be skipped and the motion data obtained in step 401 can be cached directly.

Step 404: caching the calibrated motion data at each sampling time.

The most recently obtained number N of the motion data is saved to the cache. That is, the cached motion data includes: the motion data at the latest sampling time to the motion data at the earlier N−1 sampling time. The motion data of the earliest sampling time overflows when the motion data of a new sampling time is saved to the cache. Preferably, N can be an integer of 3 or higher, and generally is an integer power of 2, such as 16 or 32 to maintain a caching length of 0.1 s~0.2 s of motion data in the cache. The data structure of the cache is a queue in the order of the sampling time, with the motion data of the latest sampling time at the end of the queue.

It should be noted that, in the embodiment the calibrated motion data is cached, but it can also be stored in any other type of storage devices.

Step 405: performing motion static detection utilizing acceleration at each of the sampling time to confirm an original time $t_o$ and an end time $t_e$ of the motion.

The original time $t_o$ is the critical sampling time from the nonmoving condition to the moving condition, and the end time $t_e$ is the critical sampling time from the moving condition to the nonmoving condition.

Judgment is performed according to predetermined motion time confirming tactics to each of the sampling time in sequence of the sampling time. If at the sampling time to the predetermined motion time confirming tactics are satisfied and at the sampling time to−1 the predetermined motion time confirming tactics are not satisfied, the sampling time to is confirmed as the original time. If at the sampling time $t_e$ the predetermined motion time confirming tactics are satisfied and at the sampling time $t_e+1$ the predetermined motion time confirming tactics are not satisfied, the sampling time $t_e$ is confirmed as the end time.

Specifically, the predetermined motion time confirming tactics may comprise: confirming one of the sampling time $t_x$ as motion time if a modulated variance $a_v$ of the acceleration from a number T of the sampling time before the sampling time $t_x$ is larger than or equal to a predetermined acceleration variance threshold and a modulated acceleration $a_o$ at the sampling time $t_x$ is larger than or equal to a predetermined motion acceleration threshold. In other words, if at a certain sampling time the predetermined motion time confirming tactics are satisfied, the sampling time is considered in a moving condition; otherwise it is considered in a nonmoving condition. T is a predetermined positive integer.

The predetermined motion time confirming tactics may effectively filter shock in a short time and prevent from a cutoff of a complete motion by short-term standstill and pause actions. The value of the predetermined acceleration variance threshold and the predetermined motion acceleration threshold can be flexible according to the degree of the motion of the recognized object. When the motion of the recognized object is more violent, the value of the predetermined acceleration variance threshold and the predetermined motion acceleration threshold can be set higher.

The sampling time between the original time $t_o$ and the end time $t_e$ in the cache is treated in sequence as the current sampling time to perform steps 406 to 411.

Step 406: confirming the original stance matrix $T_m^{bInit}$ corresponding to the geomagnetic coordinate system at the original time $t_o$ of the motion according to the motion data sampled by the tri-axial magnetometer in the cache.

$$T_m^{bInit} = [X_{bt_0}, Y_{bt_0}, Z_{bt_0}] \quad (1)$$

wherein:

$$X_{bt_0} = \begin{bmatrix} \sin(Roll_{t_0})\sin(Yaw_{t_0})\sin(Pitch_{t_0}) + \cos(Roll_{t_0})\cos(Yaw_{t_0}) \\ \sin(Roll_{t_0})\cos(Yaw_{t_0})\sin(Pitch_{t_0}) - \cos(Roll_{t_0})\sin(Yaw_{t_0}) \\ -\sin(Roll_{t_0})\cos(Pitch_{t_0}) \end{bmatrix}$$

$$Y_{bt_0} = \begin{bmatrix} \cos(Pitch_{t_0})\sin(Yaw_{t_0}) \\ \cos(Pitch_{t_0})\cos(Yaw_{t_0}) \\ \sin(Pitch_{t_0}) \end{bmatrix}, \text{ and}$$

$$Z_{bt_0} = \begin{bmatrix} \sin(Roll_{t_0})\cos(Yaw_{t_0}) - \cos(Roll_{t_0})\sin(Yaw_{t_0})\sin(Pitch_{t_0}) \\ -\sin(Roll_{t_0})\sin(Yaw_{t_0}) - \cos(Roll_{t_0})\cos(Yaw_{t_0})\sin(Pitch_{t_0}) \\ \cos(Roll_{t_0})\cos(Pitch_{t_0}) \end{bmatrix}$$

$Roll_{t_0}$, $Yaw_{t_0}$ and $Pitch_{t_0}$ are the angles sampled at the sampling time to by the tri-axial magnetometer.

Step 407: when the recognized object is in the moving condition, confirming the stance change matrix $T_{bPre}^{bCur}$ from the previous sampling time to the current sampling time according to the angular velocity data sampled at the current sampling time and the previous sampling time by the tri-axial gyroscope.

Specifically, the angular velocity data sampled by the tri-axial gyroscope at the previous sampling time is $w_P = [\omega_{Px}, \omega_{Py}, \omega_{Pz}]^T$, and the angular velocity data at the current sampling time is $w_C = [\omega_{Cx}, \omega_{Cy}, \omega_{Cz}]^T$. The time interval between adjacent sampling time is t, and the stance change matrix $T_{bPre}^{bCur}$ from the previous sampling time to the current sampling time can be confirmed as $T_{bPre}^{bCur} = R_Z R_Y R_X$.

$R_Z$, $R_Y$, $R_X$ are the stance change matrices of $\omega_P$, respectively rotating $(\omega_{Pz} + \omega_{Cz})t/2$, $(\omega_{Py} + \omega_{Cy})t/2$, and $(\omega_{Px} + \omega_{Cx})t/2$ around the Z-axis, Y-axis, and X-axis.

Step 408: confirming and recording the stance change matrix $T_{bInit}^{bCur}$ from the current time to the original time $t_o$ according to the stance change matrix $T_{bInit}^{bPre}$ from the previous time to the original time $t_o$ and the stance change matrix $T_{bPre}^{bCur}$.

In the motion with the original time $t_o$, the stance change matrix from any of the sampling time to the original time $t_o$ will be recorded. Thus, with the stance change matrix $T_{bInit}^{bPre}$ from the previous time retrieved, the stance change matrix $T_{bPre}^{bCur}$ of the current time can be:

$$T_{bInit}^{bCur} = T_{bInit}^{bPre} T_{bPre}^{bCur} \quad (2)$$

Step 409: confirming the stance matrix $T_m^{bCur}$ at the current sampling time corresponding to the three-dimensional geomagnetic coordinate system as $T_m^{bCur} = T_m^{bInit} T_{bInit}^{bCur}$.

According to the steps 407, 408 and 409, the stance matrix $T_m^{bCur}$ at the current sampling time corresponding to the three-dimensional geomagnetic coordinate system is obtained by a "feedback" type of iterative calculation, which is shown as $$T_m^{bCur} = T_m^{bInit} \prod_{x=Init}^{Cur-1} T_{b(x+1)}^{bx}.$$

The terms Cur is the current sampling time, Init is the original time $t_o$, and $T_{b(x+1)}^{bx}$ is the stance change matrix from sampling time x to sampling time x+1.

Step 410: obtaining the actual acceleration $a_m^{Mcur}$ at the current sampling time according to the formula $a_m^{Mcur} = T_m^{bCur} a^{cur} - \vec{g}$, which reduces the acceleration of gravity $\vec{g}$ from the acceleration $a^{Cur}$ at the current sampling time.

The acceleration of gravity $\vec{g}$ of the three-dimensional geomagnetic coordinate system can be obtained by a non-moving object.

Specifically, the tri-axial accelerometer can be utilized to sample a nonmoving object with M numbers of consecutive sampling time. Thus, the mean value of the acceleration of gravity obtained with the M numbers of consecutive sampling time can be the acceleration of gravity $\vec{g}$ of the three-dimensional geomagnetic coordinate system. The acceleration of gravity $\vec{g}$ can be confirmed according to formula (3):

$$\vec{g} = \frac{1}{M}\sum_{j=i}^{i+M}\vec{a}_{mj} \quad (3)$$

wherein:

M is a predetermined positive integer, i is the original sampling time for sampling of the nonmoving object, and $$\vec{a} = T_{mj}^b \vec{a}_{bj} \quad (4)$$

$\vec{a}_{bj}$ is the acceleration sampled by the tri-axial accelerometer at the sampling time j, and $T_{mj}^b$ is the stance matrix of the nonmoving object at the sampling time j. According to the angle confirmed by the trial-axial accelerometer at the sampling time j, $T_{mj}^b$ is:

$$T_{mj}^b = [X_{bj}, Y_{bj}, Z_{bj}] \quad (5)$$

wherein:

$$X_{bj} = \begin{bmatrix} \sin(Roll_j)\sin(Yaw_j)\sin(Pitch_j) + \cos(Roll_j)\cos(Yaw_j) \\ \sin(Roll_j)\cos(Yaw_j)\sin(Pitch_j) - \cos(Roll_j)\sin(Yaw_j) \\ -\sin(Roll_j)\cos(Pitch_j) \end{bmatrix}$$

$$Y_{bj} = \begin{bmatrix} \cos(Pitch_j)\sin(Yaw_j) \\ \cos(Pitch_{t_0})\cos(Yaw_j) \\ \sin(Pitch_j) \end{bmatrix}, \text{ and}$$

$$Z_{bj} = \begin{bmatrix} \sin(Roll_j)\cos(Yaw_j) - \cos(Roll_j)\sin(Yaw_j)\sin(Pitch_j) \\ -\sin(Roll_j)\sin(Yaw_j) - \cos(Roll_j)\cos(Yaw_j)\sin(Pitch_j) \\ \cos(Roll_j)\cos(Pitch_j) \end{bmatrix}$$

$Roll_j$, $Yaw_j$ and $Pitch_j$ are the angles sampled at the sampling time j by the tri-axial magnetometer.

Step 411: performing integral to the actual acceleration from the original time $t_o$ to the current sampling time to obtain the real-time velocity at the current sampling time, and performing integral to the real-time velocity from the original time $t_o$ to the current sampling time to obtain the position at the current sampling time.

The technique to obtain real-time velocity and position in the step is well-known, and description of the technique will be hereafter omitted.

Thus, at least one of the acceleration, real-time velocity and position between the original time $t_o$ and the end time $t_e$ can be saved in the database as the motion parameters of the motion.

In the aforementioned process, if the time interval between the end time of a motion and the original time of a next motion is shorter than a predetermined time period threshold, the two separate motions would be considered one continuous motion, and "connecting" of the motions must be performed. That is, if the time interval between the original time $t_o$ confirmed by the step 405 and the end time t' of the previous motion is shorter than the predetermined time period threshold, the stance matrix of t' serves as the original stance matrix $T_m^{bInit}$ at at the original time $t_o$. Otherwise, the original stance matrix $T_m^{bInit}$ at the original time $t_o$ is confirmed according to formula (1).

Figure 5:
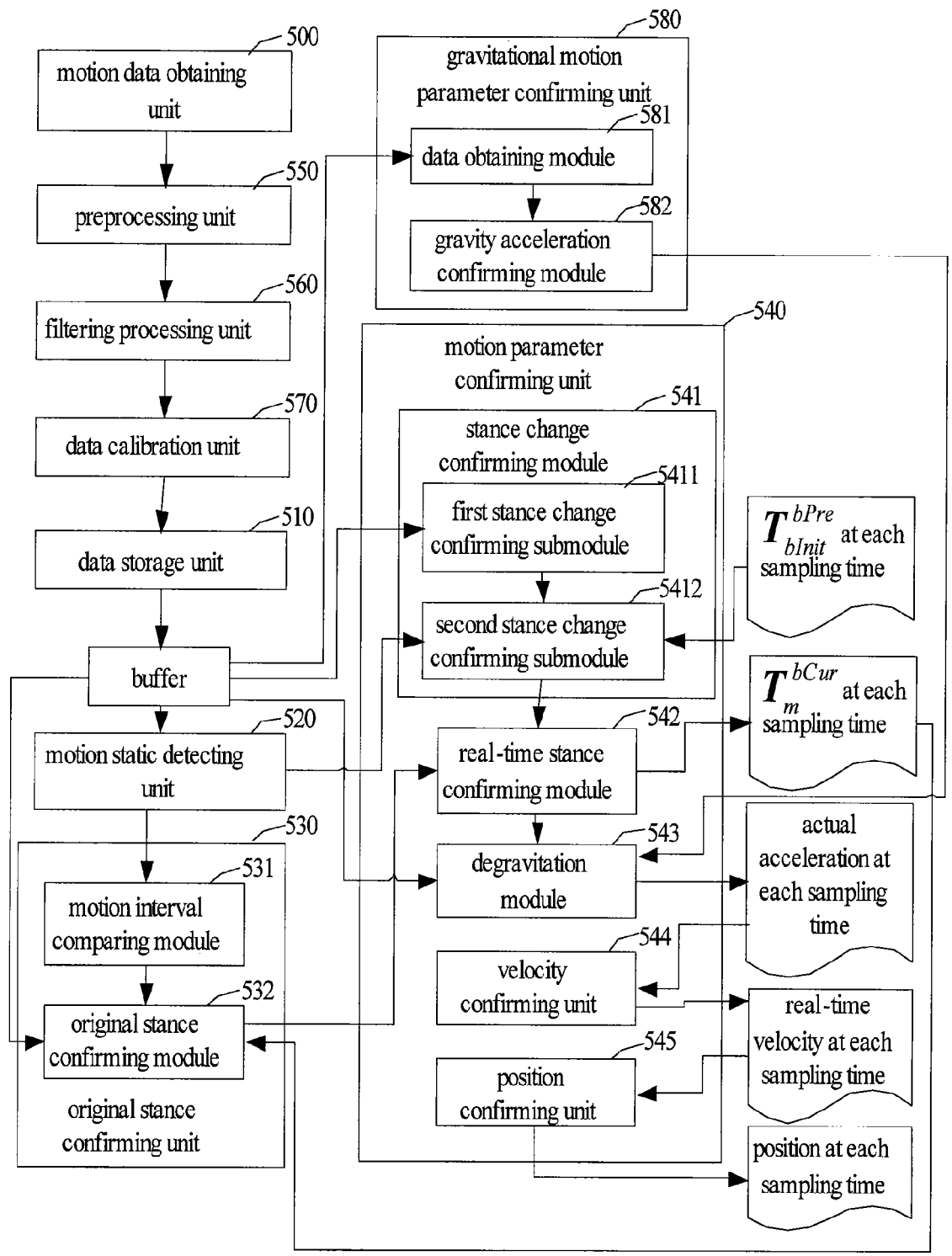
FIG. 5 is a schematic view of the structure the apparatus for confirming motion parameters in an embodiment of the disclosure.

The apparatus for confirming motion parameters corresponding to the aforementioned method of confirming motion parameters can be hereafter described in detail. As shown in FIG. 5, the apparatus comprises: a motion data obtaining unit 500, a data storage unit 510, a motion static detecting unit 520, an original stance confirming unit 530, and a motion parameter confirming unit 540.

The motion data obtaining unit 500 is configured to obtain motion data at each sampling time of a motion and send the motion data to the data storage unit 510. The motion data comprises: acceleration of a recognized object sampled by a tri-axial accelerometer, angular velocity of the recognized object sampled by a tri-axial gyroscope, and an angle of the recognized object corresponding to a three-dimensional geomagnetic coordinate system sampled by a tri-axial magnetometer.

The data storage unit 510 is configured to store the motion data.

Specifically, the data storage unit 510 stores most recently obtained number N of the motion data to a cache. N is an integer of 3 or higher, and the motion data in the cache is in an order of the sampling time with the motion data of a latest sampling time at an end of a queue in the cache. In other words, the data storage unit 510 stores motion data from the latest sampling time to the previous N−1 sampling time to the cache.

The motion static detecting unit 520 is configured to perform motion static detection utilizing the acceleration stored in the data storage unit 510 at each of the sampling time to confirm a motion original time $t_o$ and a motion end time $t_e$ of the motion.

The original stance confirming unit 530 is configured to confirm an original stance matrix $T_m^{bInit}$ corresponding to the three-dimensional geomagnetic coordinate system at the motion original time $t_o$ according to the angle stored in the data storage unit 510 at the motion original time $t_o$.

$$T_m^{bInit} = [X_{bt_0}, Y_{bt_0}, Z_{bt_0}] \qquad (1)$$

wherein:

$$X_{bt_0} = \begin{bmatrix} \sin(Roll_{t_0})\sin(Yaw_{t_0})\sin(Pitch_{t_0}) + \cos(Roll_{t_0})\cos(Yaw_{t_0}) \\ \sin(Roll_{t_0})\cos(Yaw_{t_0})\sin(Pitch_{t_0}) - \cos(Roll_{t_0})\sin(Yaw_{t_0}) \\ -\sin(Roll_{t_0})\cos(Pitch_{t_0}) \end{bmatrix}$$

$$Y_{bt_0} = \begin{bmatrix} \cos(Pitch_{t_0})\sin(Yaw_{t_0}) \\ \cos(Pitch_{t_0})\cos(Yaw_{t_0}) \\ \sin(Pitch_{t_0}) \end{bmatrix}, \text{ and}$$

$$Z_{bt_0} = \begin{bmatrix} \sin(Roll_{t_0})\cos(Yaw_{t_0}) - \cos(Roll_{t_0})\sin(Yaw_{t_0})\sin(Pitch_{t_0}) \\ -\sin(Roll_{t_0})\sin(Yaw_{t_0}) - \cos(Roll_{t_0})\cos(Yaw_{t_0})\sin(Pitch_{t_0}) \\ \cos(Roll_{t_0})\cos(Pitch_{t_0}) \end{bmatrix}$$

$Roll_{t_0}$, $Yaw_{t_0}$ and $Pitch_{t_0}$ are the angles sampled at the sampling time to by the tri-axial magnetometer.

The motion parameter confirming unit 540 is configured to confirm the acceleration at each of the sampling time by using the sampling time after the motion original time $t_o$ and before the motion end time $t_e$ sequentially as a current sampling time.

Specifically, the motion parameter confirming unit 540 comprises: a stance change confirming module 541, a real-time stance confirming module 542 and a degravitation module 543.

The stance change confirming module 541 is configured to confirm and record a stance change matrix $T_{bInit}^{bCur}$ from the current sampling time to the motion original time $t_o$ according to the angular velocity stored in the data storage unit at the current sampling time and at a previous sampling time, and a stance change matrix $T_{bInit}^{bPre}$ from the previous sampling time to the motion original time $t_o$.

The real-time stance confirming module 542 is configured to confirm a stance matrix $T_m^{bCur}$ at the current sampling time corresponding to the three-dimensional geomagnetic coordinate system as $T_m^{bCur} = T_m^{bInit} T_{bInit}^{bCur}$.

The degravitation module 543 is configured to obtain an actual acceleration $a_m^{Mcur}$ at the current sampling by adjusting the acceleration $a^{Cur}$ at the current sampling time utilizing the stance matrix $T_m^{bCur}$ to reduces an acceleration of gravity $\vec{g}$ from the acceleration $a^{Cur}$ at the current sampling time.

Furthermore, the apparatus may further comprise at least one of a preprocessing unit 550 and a filtering processing unit 560. The two units do not have a priority of process or a fixed order in processing, and processing of each unit can be performed in any sequence. FIG. 1a shows an embodiment including both units.

The preprocessing unit 550 is configured to perform interpolation processing to the motion data obtained by the motion data obtaining unit 500 and sent to the data storage unit 510. By the preprocessing unit 550, calculation accuracy in further calculation of acceleration, velocity and position can be enhanced even if the MEMS sensor does not have high sampling frequency. The interpolation processing utilized can be but not limited to linear interpolation or spline interpolation.

The filtering processing unit 560 is configured to perform filtering processing to the motion data obtained by the motion data obtaining unit 500 and sent to the data storage unit 510. Various filtering approaches can be utilized. For example, 16 point Fast Fourier Transform (FFT) filtering can be used. The specific approach of filtering is not limited.

The tri-axial accelerometer may have a problem with inaccuracy in sampling the acceleration due to the zero drift. Thus, the apparatus may further comprise a data calibration unit 570 to perform data calibration to the motion data obtained by the motion data obtaining unit 500 and sent to the data storage unit 510 utilizing a zero drift $\vec{\omega}_0$ of the tri-axial accelerometer sampling the acceleration. In other words, the acceleration obtained at each sampling time is reduced by the zero drift $\vec{\omega}_0$ to obtain the calibrated acceleration at each sampling time.

In performing motion static detection, the motion static detecting unit 520 may perform judgment according to predetermined motion time confirming tactics to each of the sampling time in sequence of the sampling time. If at the sampling time $t_o$ the predetermined motion time confirming tactics are satisfied and at the sampling time $t_o-1$ the predetermined motion time confirming tactics are not satisfied, the sampling time $t_o$ is confirmed as the motion original time; and if at the sampling time $t_e$ the predetermined motion time confirming tactics are satisfied and at the sampling time $t_e+1$ the predetermined motion time confirming tactics are not satisfied, the sampling time $t_e$ is confirmed as the motion end time.

The predetermined motion time confirming tactics can be: confirming one of the sampling time $t_x$ as motion time if a modulated variance $a_v$ of the acceleration from a number T of the sampling time before the sampling time $t_x$ is larger than or equal to a predetermined acceleration variance threshold and a modulated acceleration $a_0$ at the sampling time $t_x$ is larger than or equal to a predetermined motion acceleration threshold. The number T is a predetermined positive integer.

In an actual motion, a shock may exist during the motion period to create a temporary change of status. However, the motion is still a continuous motion. In order to deal with this problem, the original stance confirming unit 530 may further comprise a motion interval comparing module 531 and an original stance confirming module 532.

The motion interval comparing module 531 is configured to compare a time interval between the motion original time $t_o$ and a last motion original time $t'$ to a predetermined time period threshold and determine whether the time interval is shorter than the predetermined time period threshold.

The original stance confirming module 532 is configured to confirm the original stance matrix $T_m^{bInit}$ corresponding to the three-dimensional geomagnetic coordinate system at the motion original time $t_o$ according to the angle stored in the data storage unit at the motion original time to if the time interval is not shorter than the predetermined time period threshold, and to confirm a stance matrix corresponding to the three-dimensional geomagnetic coordinate system at the last motion original time $t'$ as the original stance matrix $T_m^{bInit}$ corresponding to the three-dimensional geomagnetic coordinate system at the motion original time $t_o$ if the time interval is shorter than the predetermined time period threshold.

In the apparatus, the stance change confirming module 541 may further comprise a first stance change confirming submodule 5411 and a second stance change confirming submodule 5412.

The first stance change confirming submodule 5411 is configured to confirm the stance change matrix $T_{bPre}^{bCur}$ from the previous sampling time to the current sampling time according to the angular velocity data stored at the current sampling time and at the previous sampling time in the data storage unit 510.

Specifically, the first stance change confirming submodule 5411 confirms the angular velocity data $w_P$ stored the previous sampling time is $w_P=[\omega_{Px}, \omega_{Py}, \omega_{Pz}]^T$ and the angular velocity data $w_C$ at the current sampling time is $w_C=[\omega_{Cx}, \omega_{Cy}, \omega_{Cz}]^T$, and confirms the stance change matrix $T_{bPre}^{bCur}$ from the previous sampling time to the current sampling time as $T_{bPre}^{bCur}=R_Z R_Y R_X$, wherein $R_Z$ is a stance change matrix of the angular velocity data $w_P$ rotating $(\omega_{Pz}+\omega_{Cz})t/2$ around a Z-axis, $R_Y$ is a stance change matrix of the angular velocity data $w_P$ rotating $(\omega_{Py}+\omega_{Cy})t/2$, around a Y-axis, $R_X$ is a stance change matrix of the angular velocity data $w_P$ rotating $(\omega_{Px}+\omega_{Cx})t/2$ around a X-axis, and t is a time interval between adjacent sampling time.

The second stance change confirming submodule 5412 is configured to obtain the stance change matrix $T_{bInit}^{bPre}$ from the previous sampling time to the motion original time $t_o$, and confirming a stance change matrix $T_{bInit}^{bCur}$ from the current sampling time to the motion original time $t_o$ as $T_{bInit}^{bPre} T_{bPre}^{bCur}$.

The degravitation module 543 may obtain the actual acceleration $a_m^{Mcur}$ at the current sampling time as $a_m^{Mcur}=T_m^{bCur}a^{cur}-\vec{g}$. $\vec{g}$ is the acceleration of gravity under the three-dimensional geomagnetic coordinate system.

To confirm the acceleration of gravity $\vec{g}$ under the three-dimensional geomagnetic coordinate system, the apparatus may further comprise gravitational motion parameter confirming unit 580. The gravitational motion parameter confirming unit 580 may comprise a data obtaining module 581 and a gravity acceleration confirming module 582.

The data obtaining module 581 is configured to obtain the acceleration and the angle sampled from a nonmoving object with M numbers of consecutive sampling time. That is, the tri-axial accelerometer and the tri-axial magnetometer are used to sample the nonmoving object for the data obtaining module 581 to obtain the acceleration and the angle with M numbers of consecutive sampling time.

The gravity acceleration confirming module 582 is configured to confirm the acceleration of gravity $\vec{g}$ under the three-dimensional geomagnetic coordinate system as $$\vec{g} = \frac{1}{M}\sum_{j=i}^{i+M}\vec{a}_{mj},$$

wherein M is a predetermined positive integer, i is an original sampling time for sampling of the nonmoving object, $\vec{a}_{mj}=T_{mj}^b \vec{a}_{bj}$, $\vec{a}_{bj}$ is the acceleration sampled from the nonmoving object at one of the sampling time j, and $T_{mj}^b$ is a stance matrix of the nonmoving object at the sampling time j confirmed by the angle of the nonmoving object at the sampling time j.

$$T_{mj}^b=[X_{bj},Y_{bj},Z_{bj}] \quad (5)$$

wherein:

$$X_{bj} = \begin{bmatrix} \sin(Roll_j)\sin(Yaw_j)\sin(Pitch_j) + \cos(Roll_j)\cos(Yaw_j) \\ \sin(Roll_j)\cos(Yaw_j)\sin(Pitch_j) - \cos(Roll_j)\sin(Yaw_j) \\ -\sin(Roll_j)\cos(Pitch_j) \end{bmatrix}$$

$$Y_{bj} = \begin{bmatrix} \cos(Pitch_j)\sin(Yaw_j) \\ \cos(Pitch_{t_0})\cos(Yaw_j) \\ \sin(Pitch_j) \end{bmatrix}, \text{ and}$$

$$Z_{bj} = \begin{bmatrix} \sin(Roll_j)\cos(Yaw_j) - \cos(Roll_j)\sin(Yaw_j)\sin(Pitch_j) \\ -\sin(Roll_j)\sin(Yaw_j) - \cos(Roll_j)\cos(Yaw_j)\sin(Pitch_j) \\ \cos(Roll_j)\cos(Pitch_j) \end{bmatrix}$$

$Roll_j$, $Yaw_j$ and $Pitch_j$ are the angles sampled at the sampling time j by the tri-axial magnetometer.

After confirmation of the actual acceleration at each sampling time, the actual velocity and position can be then confirmed. Thus, the motion parameter confirming unit 540 may further comprise a velocity confirming unit 544 and a position confirming unit 545.

The velocity confirming unit 544 is configured to obtain a real-time velocity at the current sampling time by performing integral to the actual acceleration $a_m^{Mcur}$ from the motion original time $t_o$ to the current sampling time.

The position confirming unit 545 is configured to obtain a position at the current sampling time by performing integral to the real-time velocity from the motion original time $t_o$ to the current sampling time.

At least one of the acceleration, real-time velocity and position at each sampling time between the motion original time $t_o$ to the motion end time $t_e$ is stored in the database as the motion parameters of the motion.

After the motion parameters are confirmed by the process shown in FIG. 4 and the apparatus in FIG. 5, further application can be described as follows:

(1) The motion parameters of the motion, such as information of acceleration, velocity and position, can be sent to a motion recognizing device (such as the motion recognizing device 140 in FIG. 1*a*). The motion recognizing device can recognize the motion type of the motion according to the motion parameters, and thus extracting a part of the motion parameters corresponding to a certain type of sport motion. For example, the MEMS sensor can be disposed on a golf glove, and the method and apparatus of the present disclosure can be utilized to confirm the motion parameters of the golf glove. These motion parameters are then provided to the motion recognizing device. As it is possible that the golfer may do something other than the swing motion, such as drinking water, taking a rest, or picking up a phone call, the motion recognizing device may recognize and extract the part of motion parameters corresponding to a full golf swing.

(2) The motion parameters such as velocity or position can be sent to a parameter display device (such as the parameter display device 150 in FIG. 1*a*). The parameter display device can display the position information at each sampling time in the format of a table, or display a three-dimensional motion path of the recognized object, and/or display the velocity information at each sampling time in the format of a table or display the velocity information of the recognized object in a line chart. A user can check the detailed information of the motion of the recognized object, such as real-time velocity, position, position-time distribution, and velocity-time distribution, by the parameter display device.

(3) The motion parameters of the motion can be sent to an expert evaluation device, or the information displayed on the parameter display device can be provided to the expert evaluation device for evaluation. The expert evaluation device can be a device performing automated evaluation according to preset motion parameter database. The preset motion parameter database stores evaluation information corresponding to the motion parameters, and can provide evaluation for information such as acceleration, real-time velocity and position at each time. The expert evaluation device can also be a user interface to provide the motion parameters to the expert for human evaluation. Preferably, the user interface can obtain the evaluation information input by the expert, and the evaluation information can be sent to a terminal device for the user to check for reference.

(4) The motion parameters of the motion can be sent to more than one terminal device, such as the iPhones of more than one users. Thus, the users of the terminal devices can share the motion parameters to create interaction.

It should be noted that, in the embodiments of the invention, the MEMS sensor device is provided as an example of the sensor device. However, the invention is not limited to the MEMS sensor device, and other sensor device can be utilized to perform sampling of the motion data in the embodiments of the invention.

The preferred embodiments of the present invention have been disclosed in the examples to show the applicable value in the related industry. However the examples should not be construed as a limitation on the actual applicable scope of the invention, and as such, all modifications and alterations without departing from the spirits of the invention and appended claims shall remain within the protected scope and claims of the invention.

What is claimed is:

1. A method of ball game motion recognition, comprising:
  obtaining and storing motion data at each sampling time, the motion data comprising:
    acceleration of a recognized object, angular velocity of the recognized object, and an angle of the recognized object corresponding to a three-dimensional geomagnetic coordinate system;
  performing motion static detection utilizing the acceleration stored at each of the sampling time to confirm a motion original time $t_o$ and a motion end time $t_e$ of a motion;
  confirming an original stance matrix $T_m^{bInit}$ corresponding to the three-dimensional geomagnetic coordinate system at the motion original time $t_o$ according to the angle stored at the motion original time $t_o$; and
  using each of the sampling time sequentially as a current sampling time to perform the steps of:
    confirming and recording a stance change matrix $T_{bInit}^{bCur}$ from the current sampling time to the motion original time $t_o$ according to the angular velocity stored at the current sampling time and at a previous sampling time, and a stance change matrix $T_{bInit}^{bPre}$ from the previous sampling time to the motion original time $t_o$;
    confirming a stance matrix $T_m^{bCur}$ at the current sampling time corresponding to the three-dimensional geomagnetic coordinate system as $T_m^{bCur} = T_m^{bInit} T_{bInit}^{bCur}$; and
    obtaining an actual acceleration $a_m^{Mcur}$ at the current sampling time by adjusting the acceleration $a^{Cur}$ at the current sampling time utilizing the stance matrix $T_m^{bCur}$ to reduces an acceleration of gravity $\vec{g}$ from the acceleration $a^{Cur}$ at the current sampling time.

2. The method as claimed in claim 1, further comprising, after obtaining and before storing the motion data at each sampling time, at least one of:
  performing interpolation processing to the motion data obtained at each of the sampling time; and
  performing filtering processing to the motion data obtained at each of the sampling time.

3. The method as claimed in claim 1, further comprising, after obtaining and before storing the motion data at each sampling time:
  performing data calibration to the motion data at each of the sampling time utilizing a zero drift $\vec{\omega}_0$ of a tri-axial accelerometer sampling the acceleration.

4. The method as claimed in claim 1, wherein the storing of the motion data further comprises:
  storing most recently obtained number N of the motion data to a cache;

wherein N is an integer of 3 or higher, and the motion data in the cache is in an order of the sampling time with the motion data of a latest sampling time at an end of a queue in the cache.

5. The method as claimed in claim 1, wherein performing motion static detection further comprises:

performing judgment according to predetermined motion time confirming tactics to each of the sampling time in sequence of the sampling time, if at the sampling time $t_o$ the predetermined motion time confirming tactics are satisfied and at the sampling time $t_o-1$ the predetermined motion time confirming tactics are not satisfied, confirming the sampling time $t_o$ as the motion original time; and if at the sampling time $t_e$ the predetermined motion time confirming tactics are satisfied and at the sampling time $t_e+1$ the predetermined motion time confirming tactics are not satisfied, confirming the sampling time $t_e$ as the motion end time.

6. The method as claimed in claim 5, wherein the predetermined motion time confirming tactics comprises:

confirming one of the sampling time $t_x$ as motion time if a modulated variance $a_v$ of the acceleration from a number T of the sampling time before the sampling time $t_x$ is larger than or equal to a predetermined acceleration variance threshold and a modulated acceleration $a_0$ at the sampling time $t_x$ is larger than or equal to a predetermined motion acceleration threshold, wherein the number T is a predetermined positive integer.

7. The method as claimed in claim 1, further comprising, before confirming an original stance matrix $T_m^{bInit}$:

comparing a time interval between the motion original time $t_o$ and a last motion original time $t'$ to a predetermined time period threshold, and if the time interval is shorter than the predetermined time period threshold, confirming a stance matrix corresponding to the three-dimensional geomagnetic coordinate system at the last motion original time $t'$ as the original stance matrix $T_m^{bInit}$ corresponding to the three-dimensional geomagnetic coordinate system at the motion original time $t_o$, and not confirming an original stance matrix.

8. The method as claimed in claim 1, wherein confirming and recording a stance change matrix $T_{bInit}^{bCur}$ further comprises:

confirming the stance change matrix $T_{bPre}^{bCur}$ from the previous sampling time to the current sampling time according to the angular velocity data stored at the current sampling time and at the previous sampling time; and obtaining the stance change matrix $T_{bInit}^{bPre}$ from the previous sampling time to the motion original time $t_o$, and confirming a stance change matrix $T_{bInit}^{bCur}$ from the current sampling time to the motion original time $t_o$ as $T_{bInit}^{bCur} = T_{bInit}^{bPre} T_{bPre}^{bCur}$.

9. The method as claimed in claim 8, wherein the step S411 further comprises:

confirming the angular velocity data $w_P$ stored the previous sampling time is $w_P = [\omega_{Px}, \omega_{Py}, \omega_{Pz}]^T$ and the angular velocity data $w_C$ at the current sampling time is $w_C = [\omega_{Cx}, \omega_{Cy}, \omega_{Cz}]^T$; and confirming the stance change matrix $T_{bPre}^{bCur}$ from the previous sampling time to the current sampling time as $T_{bPre}^{bCur} = R_Z R_Y R_X$, wherein $R_Z$ is a stance change matrix of the angular velocity data $w_P$ rotating $(\omega_{Pz} + \psi_{Cz})t/2$ around a Z-axis, $R_Y$ is a stance change matrix of the angular velocity data $w_P$ rotating $(\omega_{Py} + \omega_{Cy})t/2$, around a Y-axis, $R_X$ is a stance change matrix of the angular velocity data $w_P$ rotating $(\omega_{Px} + \omega_{Cx})t/2$ around a X-axis, and t is a time interval between adjacent sampling time.

10. The method as claimed in claim 1, wherein obtaining an actual acceleration further comprises:

obtaining the actual acceleration $a_m^{Mcur}$ at the current sampling time as $a_m^{Mcur} = T_m^{bCur} a^{cur} - \vec{g}$, wherein $\vec{g}$ is the acceleration of gravity under the three-dimensional geomagnetic coordinate system.

11. The method as claimed in claim 10, wherein the acceleration of gravity $\vec{g}$ can be confirmed by:

obtaining the acceleration and the angle sampled from a nonmoving object with M numbers of consecutive sampling time; and confirming the acceleration of gravity $\vec{g}$ under the three-dimensional geomagnetic coordinate system as $$\vec{g} = \frac{1}{M} \sum_{j=i}^{i+M} \vec{a}_{mj};$$

wherein M is a predetermined positive integer, i is an original sampling time for sampling of the nonmoving object, $\vec{a}_{mj} = T_{mj}^b \vec{a}_{bj}$, $\vec{a}_{bj}$ is the acceleration sampled from the nonmoving object at one of the sampling time j, and $T_{mj}^b$ is a stance matrix of the nonmoving object at the sampling time j confirmed by the angle of the nonmoving object at the sampling time j.

12. The method as claimed in claim 1, further comprising, after obtaining an actual acceleration:

performing integral to the actual acceleration $a_m^{Mcur}$ from the motion original time $t_o$ to the current sampling time to obtain a real-time velocity at the current sampling time, and performing integral to the real-time velocity from the motion original time $t_o$ to the current sampling time to obtain a position at the current sampling time.

13. An apparatus for confirming motion parameters, comprising:

a motion data obtaining unit to obtain motion data at each sampling time of a motion, the motion data comprising: acceleration of a recognized object sampled by a tri-axial accelerometer, angular velocity of the recognized object sampled by a tri-axial gyroscope, and an angle of the recognized object corresponding to a three-dimensional geomagnetic coordinate system sampled by a tri-axial magnetometer;

a data storage unit to store the motion data;

a motion static detecting unit to perform motion static detection utilizing the acceleration stored in the data storage unit at each of the sampling time to confirm a motion original time $t_o$ and a motion end time $t_o$ of the motion;

an original stance confirming unit to confirm an original stance matrix $T_m^{bInit}$ corresponding to the three-dimensional geomagnetic coordinate system at the motion original time $t_o$ according to the angle stored in the data storage unit at the motion original time $t_o$; and a motion parameter confirming unit to confirm the acceleration at each of the sampling time by using the sampling time after the motion original time $t_o$ and before the motion end time $t_o$ sequentially as a current sampling time;

wherein the motion parameter confirming unit comprises:
  a stance change confirming module to confirm and record a stance change matrix $T_b^{bCur}$ from the current sampling time to the motion original time $t_o$ according to the angular velocity stored in the data storage unit at the current sampling time and at a previous sampling time, and a stance change matrix $T_{bInit}^{bPre}$ from the previous sampling time to the motion original time $t_o$;
  a real-time stance confirming module to confirm a stance matrix $T_m^{bCur}$ at the current sampling time corresponding to the three-dimensional geomagnetic coordinate system as $T_m^{bCur}=T_m^{bInit}T_{bInit}^{bCur}$; and
  a degravitation module to obtain an actual acceleration $a_m^{Mcur}$ at the current sampling time by adjusting the acceleration $a^{Cur}$ at the current sampling time utilizing the stance matrix $T_m^{bCur}$ to reduces an acceleration of gravity $\vec{g}$ from the acceleration $a^{Cur}$ at the current sampling time.

14. The apparatus as claimed in claim 13, further comprising at least one of a preprocessing unit and a filtering processing unit, wherein:
  the preprocessing unit is configured to perform interpolation processing to the motion data obtained by the motion data obtaining unit and sent to the data storage unit; and
  the filtering processing unit is configured to perform filtering processing to the motion data obtained by the motion data obtaining unit and sent to the data storage unit.

15. The apparatus as claimed in claim 13, further comprising a data calibration unit to perform data calibration to the motion data obtained by the motion data obtaining unit and sent to the data storage unit utilizing a zero drift $\vec{\omega}_o$ of the tri-axial accelerometer sampling the acceleration.

16. The apparatus as claimed in claim 13, wherein the data storage unit stores most recently obtained number N of the motion data to a cache, wherein N is an integer of 3 or higher, and the motion data in the cache is in an order of the sampling time with the motion data of a latest sampling time at an end of a queue in the cache.

17. The apparatus as claimed in claim 13, wherein the motion static detecting unit performs judgment according to predetermined motion time confirming tactics to each of the sampling time in sequence of the sampling time, and if at the sampling time $t_o$ the predetermined motion time confirming tactics are satisfied and at the sampling time $t_o-1$ the predetermined motion time confirming tactics are not satisfied, the sampling time $t_o$ is confirmed as the motion original time; and if at the sampling time $t_e$ the predetermined motion time confirming tactics are satisfied and at the sampling time $t_e+1$ the predetermined motion time confirming tactics are not satisfied, the sampling time $t_e$ is confirmed as the motion end time.

18. The apparatus as claimed in claim 17, wherein the predetermined motion time confirming tactics comprises:
  confirming one of the sampling time $t_x$ as motion time if a modulated variance $a_v$ of the acceleration from a number T of the sampling time before the sampling time $t_x$ is larger than or equal to a predetermined acceleration variance threshold and a modulated acceleration $a_0$ at the sampling time $t_x$ is larger than or equal to a predetermined motion acceleration threshold, wherein the number T is a predetermined positive integer.

19. The apparatus as claimed in claim 13, wherein the original stance confirming unit comprises:
  a motion interval comparing module to compare a time interval between the motion original time $t_o$ and a last motion original time t' to a predetermined time period threshold; and
  an original stance confirming module to confirm the original stance matrix $T_m^{bInit}$ corresponding to the three-dimensional geomagnetic coordinate system at the motion original time $t_o$ according to the angle stored in the data storage unit at the motion original time $t_o$ if the time interval is not shorter than the predetermined time period threshold, and to confirm a stance matrix corresponding to the three-dimensional geomagnetic coordinate system at the last motion original time t' as the original stance matrix $T_m^{bInit}$ corresponding to the three-dimensional geomagnetic coordinate system at the motion original time $t_o$ if the time interval is shorter than the predetermined time period threshold.

20. The apparatus as claimed in claim 13, wherein the stance change confirming module comprises:
  a first stance change confirming submodule to confirm the stance change matrix $T_{bPre}^{bCur}$ from the previous sampling time to the current sampling time according to the angular velocity data stored at the current sampling time and at the previous sampling time; and
  a second stance change confirming submodule to obtain the stance change matrix $T_{bInit}^{bPre}$ from the previous sampling time to the motion original time $t_o$, and confirming a stance change matrix $T_{bInit}^{bCur}$ from the current sampling time to the motion original time $t_o$ as $T_{bInit}^{bCur}=T_{bInit}^{bPre}T_{bPre}^{bCur}$.

21. The apparatus as claimed in claim 20, wherein the first stance change confirming submodule confirms the angular velocity data $w_P$ stored the previous sampling time is $w_P=[\omega_{Px},\omega_{Py},\omega_{Pz}]^T$ and the angular velocity data $w_C$ at the current sampling time is $w_C=[\omega_{Cx},\omega_{Cy},\omega_{Cz}]^T$, and confirms the stance change matrix $T_{bPre}^{bCur}$ from the previous sampling time to the current sampling time as $T_{bPre}^{bCur}=R_ZR_YR_X$, wherein $R_Z$ is a stance change matrix of the angular velocity data $w_P$ rotating $(\omega_{Pz}+\omega_{Cz})t/2$ around a Z-axis, $R_Y$ is a stance change matrix of the angular velocity data $w_P$ rotating $(\omega_{Py}+\omega_{Cy})t/2$, around a Y-axis, $R_X$ is a stance change matrix of the angular velocity data $w_P$ rotating $(\omega_{Px}+\omega_{Cx})t/2$ around a X-axis, and t is a time interval between adjacent sampling time.

22. The apparatus as claimed in claim 13, wherein the degravitation module obtains the actual acceleration $a_m^{Mcur}$ at the current sampling time as $a_m^{Mcur}=T_m^{bCur}a^{cur}-\vec{g}$, wherein $\vec{g}$ is the acceleration of gravity under the three-dimensional geomagnetic coordinate system.

23. The apparatus as claimed in claim 22, further comprising a gravitational motion parameter confirming unit, wherein the gravitational motion parameter confirming unit comprises:
  a data obtaining module to obtain the acceleration and the angle sampled from a nonmoving object with M numbers of consecutive sampling time; and
  a gravity acceleration confirming module to confirm the acceleration of gravity $\vec{g}$ under the three-dimensional geomagnetic coordinate system as $$\vec{g} = \frac{1}{M}\sum_{j=i}^{i+M}\vec{a}_{mj},$$

wherein M is a predetermined positive integer, i is an original sampling time for sampling of the nonmoving object, $\vec{a}_{mj}=T_{mj}^b\vec{a}_{bj}$, $\vec{a}_{bj}$ is the acceleration sampled from the nonmoving object at one of the sampling time j, and $T_{mj}^{b}$ is a stance matrix of the nonmoving object at the sampling time j confirmed by the angle of the nonmoving object at the sampling time j.

24. The apparatus as claimed in claim 13, wherein the motion parameter confirming unit further comprises:
   a velocity confirming unit to obtain a real-time velocity at the current sampling time by performing integral to the actual acceleration $a_m^{Mcur}$ from the motion original time $t_o$ to the current sampling time, and
   a position confirming unit to obtain a position at the current sampling time by performing integral to the real-time velocity from the motion original time $t_o$ to the current sampling time.

25. A motion assisting device, comprising:
   an apparatus for confirming motion parameters as claimed in claim 13; and
   a sensor device to sample the motion data of the recognized object at each of the sampling time, the motion data comprising: the acceleration of the recognized object, the angular velocity of the recognized object, and the angle of the recognized object corresponding to a three-dimensional geomagnetic coordinate system.

26. The motion assisting device as claimed in claim 25, wherein the sensor device comprises:
   a tri-axial accelerometer to sample the acceleration of the recognized object;
   a tri-axial gyroscope to sample the angular velocity of the recognized object; and
   a tri-axial magnetometer to sample the angle of the recognized object corresponding to a three-dimensional geomagnetic coordinate system.

27. The motion assisting device as claimed in claim 25, further comprising:
   a processor to retrieve and transmit the motion data from the sensor device to the motion parameter confirming device according to predetermined transfer protocol.

28. The motion assisting device as claimed in claim 25, further comprising:
   data transmit interface to send motion parameters of the predetermined ball game type recognized by the apparatus for ball game motion recognition to a peripheral device.

29. The method of claim 1, further comprising confirming an original stance matrix $T_m^{bInit}$ corresponding to the three-dimensional geomagnetic coordinate system at the motion original time $t_o$ according to the angle stored at the motion original time $t_o$.

* * * * *